(12) United States Patent
Slodowski et al.

(10) Patent No.: US 7,277,190 B2
(45) Date of Patent: Oct. 2, 2007

(54) MEASUREMENT SYSTEM WITH AN OPTICAL MEASUREMENT ARRANGEMENT

(75) Inventors: Matthias Slodowski, Jena (DE); Detlef Wolter, Jenapriessnitz (DE)

(73) Assignee: Vistec Semiconductor Systems Jena GmbH, Jena (DE)

( * ) Notice: Subject to any disclaimer, the term of this patent is extended or adjusted under 35 U.S.C. 154(b) by 470 days.

(21) Appl. No.: 10/780,759

(22) Filed: Feb. 19, 2004

(65) Prior Publication Data

US 2004/0169868 A1 Sep. 2, 2004

(30) Foreign Application Priority Data

Mar. 1, 2003 (DE) ................................. 103 09 033

(51) Int. Cl.
*G01B 11/28* (2006.01)
*G01N 21/86* (2006.01)
*G01V 8/00* (2006.01)
*B60Q 3/04* (2006.01)
*F21V 1/00* (2006.01)
*F21V 11/00* (2006.01)
*F21V 15/00* (2006.01)

(52) U.S. Cl. .................. 356/630; 250/559.27; 362/240; 362/362

(58) Field of Classification Search ...................... None
See application file for complete search history.

(56) References Cited

U.S. PATENT DOCUMENTS

| | | | | |
|---|---|---|---|---|
| 1,393,675 A | * | 10/1921 | Doe | ........................... 362/200 |
| 2,301,401 A | * | 11/1942 | Hennessy et al. | ........... 250/239 |
| 2,778,872 A | * | 1/1957 | Nyman | ...................... 358/495 |
| 3,035,481 A | * | 5/1962 | Jones et al. | ................... 356/41 |
| 3,358,134 A | * | 12/1967 | Gonyea | ...................... 362/484 |
| 3,417,392 A | * | 12/1968 | Hansen, Sr. et al. | ........ 340/515 |
| 4,005,286 A | * | 1/1977 | Faulkner | ..................... 250/216 |
| 4,051,365 A | * | 9/1977 | Fukuyama et al. | ...... 250/222.1 |
| 5,696,609 A | | 12/1997 | Cresens et al. | |
| 5,860,720 A | | 1/1999 | Negishi et al. | |
| 6,456,373 B1 | | 9/2002 | Wienecke et al. | |
| 6,502,969 B2 | * | 1/2003 | Logel et al. | ................. 362/490 |
| 2002/0122178 A1 | * | 9/2002 | McMurtry et al. | .......... 356/401 |

* cited by examiner

*Primary Examiner*—Gregory J. Toatley, Jr.
*Assistant Examiner*—Gordon J. Stock, Jr.
(74) *Attorney, Agent, or Firm*—Foley & Lardner LLP

(57) ABSTRACT

The invention concerns an optical measurement arrangement, in particular for the examination of layer systems, and can include an illumination device having at least one illumination source for delivering a measurement light beam and coupling the measurement light beam into the beam path of a layer thickness measuring instrument. In such a measurement arrangement, the illumination device can be housed in a lamp housing that may be detachably connected to the remaining portion of the measurement arrangement via an installation element wherein illumination sources can be prealigned with respect to the beam path.

9 Claims, 5 Drawing Sheets

MEASUREMENT SYSTEM WITH AN OPTICAL MEASUREMENT ARRANGEMENT

CROSS REFERENCE TO RELATED APPLICATIONS

This application claims priority of the German patent application 103 09 033.9 which is incorporated by reference herein.

FIELD OF THE INVENTION

The invention refers to an optical measurement arrangement defining at least one illumination beam path, in particular for the examination of systems of thin layers.

BACKGROUND OF THE INVENTION

High reliability is essential in instruments that are used for dimensional consistency monitoring in continuous fabrication lines—for example, for layer thickness measurement in the context of wafer manufacture in semiconductor production—since information about product quality and the stability of the production process is obtained on the basis of the measurement results. This requires that the accuracy of the measuring instrument technology used be stable.

Fundamentally, the accuracy of optical measurement arrangements depends to a considerable degree on consistent parameters of the measurement light that is generated in an illumination device. The long-term stability of the lamps used for this purpose has a great influence on the quality of the measurement arrangement. The service life of the lamps is limited, however, and as they age they become unsuitable for measurement purposes and must be replaced after a certain time. Replacement of the lamps must normally be accomplished at the site of the measurement arrangement by technicians of the manufacturer or a maintenance company, since a newly installed lamp must first be aligned with respect to the beam path in a complex operation; the reason is that a lamp that is even slightly misaligned can considerably degrade the performance of the measurement arrangement.

For the customer, this on the one hand is very time-consuming because the time period from failure of the lamp to notification of the technician (possibly not available locally) and alignment of the new lamp is in some circumstances very long, and during that period the lamp cannot be used. On the other hand, this type of lamp replacement is very cost-intensive.

U.S. Pat. No. 6,456,373 discloses an apparatus for monitoring the emitted light for such measurement arrangements, in which the lamps are automatically exchanged when the light no longer conforms to the necessary requirements in terms of measurement accuracy. This apparatus is, however, very expensive to acquire and is susceptible to failure because of its complex mechanism.

Simple apparatuses having manually replaceable lamp housings are described in the existing art, for example in U.S. Pat. No. 5,696,609 for flatbed scanners and in U.S. Pat. No. 5,860,720 for illumination of an LCD rear projector. No particularly stringent requirements in terms of illumination or alignment of the optics are imposed in these arrangements, however, since the light is not used for measurements and the arrangements thus react less sensitively to slight misalignments.

Although U.S. Pat. No. 5,696,609 indicates that provision is made for an optical alignment of the illumination module once the illumination sources have been preinstalled in the lamp housing at the factory, it leaves open the manner in which this occurs. All that is stated in the description of FIGS. 14a and 14b (columns 11-12) is that the scanner possesses an access panel. When the panel is open, the illumination module with the already-aligned illumination sources can be inserted into or removed from the scanner.

The lamp housing for illumination of an LCD rear projector described in U.S. Pat. No. 5,860,720 is inserted into an opening provided for it in the housing of the projector, and secured therein with screws. In this case as well, the illumination device is aligned with respect to the optics within predetermined tolerances, but in both cases the tolerances are much greater than would be reliable in the case of an optical measurement arrangement, where the tolerance is approximately 10 μm.

SUMMARY OF THE INVENTION

It is thus the object of the invention to develop further an optical measurement arrangement so as to make possible replacement of the illumination sources in a manner that is more economical and less time-consuming for the user than with hitherto known optical measurement arrangements.

According to the present invention, this object is achieved in that an optical measurement arrangement defining at least one illumination beam path, in particular for the examination of systems of thin layers, comprises:
  a lamp housing having at least one illumination source for delivering at least one measurement light beam into the illumination beam path of the optical measurement arrangement, and
  an installation element connecting the lamp housing detachably to the optical measurement arrangement, wherein the at least one illumination source is pre-aligned in the lamp housing, so that the measurement light beam of the at least one illumination source coincides with the at least one illumination beam path of the optical measurement arrangement.

Instead of replacing only one lamp, the entire lamp housing—which often also contains two lamps (a halogen and a deuterium lamp) in order to cover the widest possible spectrum—is replaced. The new lamp housing can then immediately be connected via the installation element to the remaining portion of the measurement arrangement. The lamps in this lamp housing have already been prealigned, so that in this case alignment is no longer necessary. The measurement arrangement is therefore ready for use again in a very short time. The prealignment can be accomplished, for example, at the premises of the manufacturer or of a company having a maintenance contract.

The lamp housing with the defective lamp is transferred to the manufacturer or the maintenance firm, where one or both lamps are replaced and a new alignment is performed. The lamp housing with the aligned lamps is then made available again to the user.

In order simplify connection to and detachment from the remaining portion of the measurement arrangement, a notch and a stop are preferably provided on the installation element. Two sockets are mounted on the lamp housing, of which one coacts with the notch and the other with the stop. With this, a guidance system that is configured e.g. as a plain guide is implemented immediately upon insertion of a new lamp housing. In this fashion the connection can be very easily made and equally easily unmade again.

In an advantageous embodiment of the invention, a first contact in the form of a socket and a second contact in the form of a pin are provided in order to create an electrical contact between the lamp housing and the remaining portion of the measurement arrangement. This integration of the electrical contacts into the coupling device makes it possible to dispense with a separate cable for the lamp housing, which makes the lamp housing easier to handle.

It is advisable for at least one socket of the lamp housing to be equipped with a pin that coacts with a surface of the installation element. This results in a further positional retention of the lamp housing.

Advantageously, a limiting stop connected to the pin is provided in order to limit movement in the guidance direction. A number of possible configurations are conceivable in this context. If the socket is embodied, for example, as a tube (i.e. open at both ends) and is mounted in easily accessible fashion on the measurement arrangement, and if the connection between the limiting stop and the pin is embodied as an insertion connection or a threaded connection, then the limiting stop is first removed. The connection between the lamp housing and the measurement arrangement is then made, for which purpose the pin is inserted into the socket and the lamp housing is slid along that guide in the direction of the remaining portion of the measurement arrangement. The connection between the pin and the limiting stop is then reestablished. An opening in the socket, through which the limiting stop can be inserted or threaded into a matching opening in the pin, can be provided, for example, for this purpose. Another possibility is to make the pin longer than the socket and to provide the opening in the pin for the limiting stop in the protruding portion of the pin, so as to prevent any relative movement between the pin and the socket when the limiting stop is inserted. In this case, however, the pin only prevents the lamp housing from being pulled out. Further means are necessary in order to suppress the relative movement entirely; for example, the lamp housing can be inserted sufficiently far that the side of the lamp housing on which the pin is mounted is in contact with the remaining portion of the measurement arrangement, and the lamp housing cannot be slid further in that direction.

The limiting stop can also be connected to the pin by means of a spring. Before the connection between the lamp housing and the measurement arrangement is created, i.e. upon insertion, the limiting stop is first pushed (for example, by hand) into the pin, and jumps back out when the lamp housing is inserted correctly.

To minimize the number of connecting and structural elements required, it is useful to configure the pin as a hollow cylinder, open at both ends, for transmission of the light proceeding from the illumination source.

The guidance system need not necessarily comprise a socket and a pin, however. Other guidance systems are also conceivable. For example, the guidance system can also be configured as a dovetail guide having at least one slide bar. The slide bar is advantageously equipped with a limiting stop for limiting movement in the guidance direction. A guidance system of this kind is particularly suitable for vertical arrangements, i.e. if the lamp housing is to be inserted from above into the rest of the measurement arrangement.

It should be indicated at this juncture that the embodiments of the guidance system described here are merely exemplary in nature, and that further embodiments of guidance systems known in the existing art are likewise usable. Those coupling devices in which detachment and connection of the lamp housing and the remaining portion of the measurement arrangement can be effected with few technical resources are especially advantageous.

It is advantageous that a first and a second hollow cylinder, through which light is guidable from the illumination sources in the lamp housing to the measurement arrangement, are guided respectively in the first and the second socket. The installation element in the measurement arrangement comprises a block in which the notch and the stop are embodied. Also provided is a plate that presses the first and the second socket immovably onto the notch and into the stop.

BRIEF DESCRIPTION OF THE DRAWINGS

The invention will be described below with reference to an example. In the drawings associated therewith.

DETAILED DESCRIPTION OF THE INVENTION

Figure 1A:
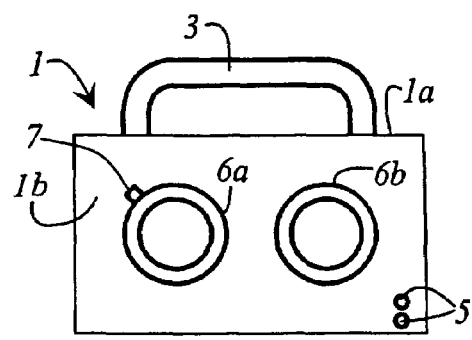
FIG. 1a is a schematic front view of the lamp housing.
Figure 1B:
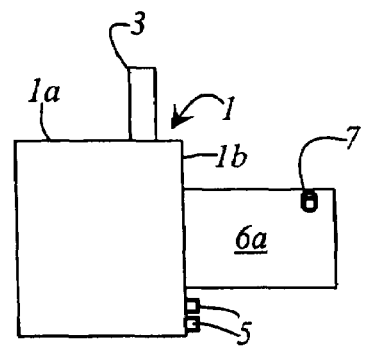
FIG. 1b is a schematic side view of the lamp housing.
Figure 1C:
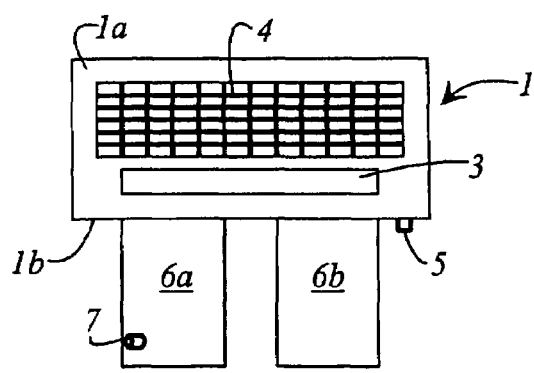
FIG. 1c is a schematic plan view of the lamp housing.

FIG. 1a is a front view of lamp housing 1, i.e. showing the side that, in the connected state, faces toward remaining portion 2 (cf. FIG. 2) of the measurement arrangement. FIG. 1b is a side view of lamp housing 1, and FIG. 1c a plan view of lamp housing 1. A handle 3 is mounted on an upper side 1a of lamp housing 1 to improve handling and transportability. Also provided on the upper side of lamp housing 1 is a ventilation grid 4 to discharge the heat that is produced during operation of the illumination sources (not depicted) provided in the interior of lamp housing 1.

Additionally mounted on a front side 1b of lamp housing 1 is at least one contact 5 in the form of a pin, for creating an electrical contact between lamp housing 1 and remaining portion 2 of the measurement arrangement. First and second hollow cylinders 6a and 6b are moreover connected to front side 1b of lamp housing 1. Through hollow cylinders 6a and 6b, light is transmitted from two illumination sources present in lamp housing 1, for example a deuterium lamp and a halogen lamp, to remaining portion 2 of the measurement arrangement. A limiting stop 7 is connected to first hollow cylinder 6a, for example via an insertion connection or threaded connection.

Figure 2:
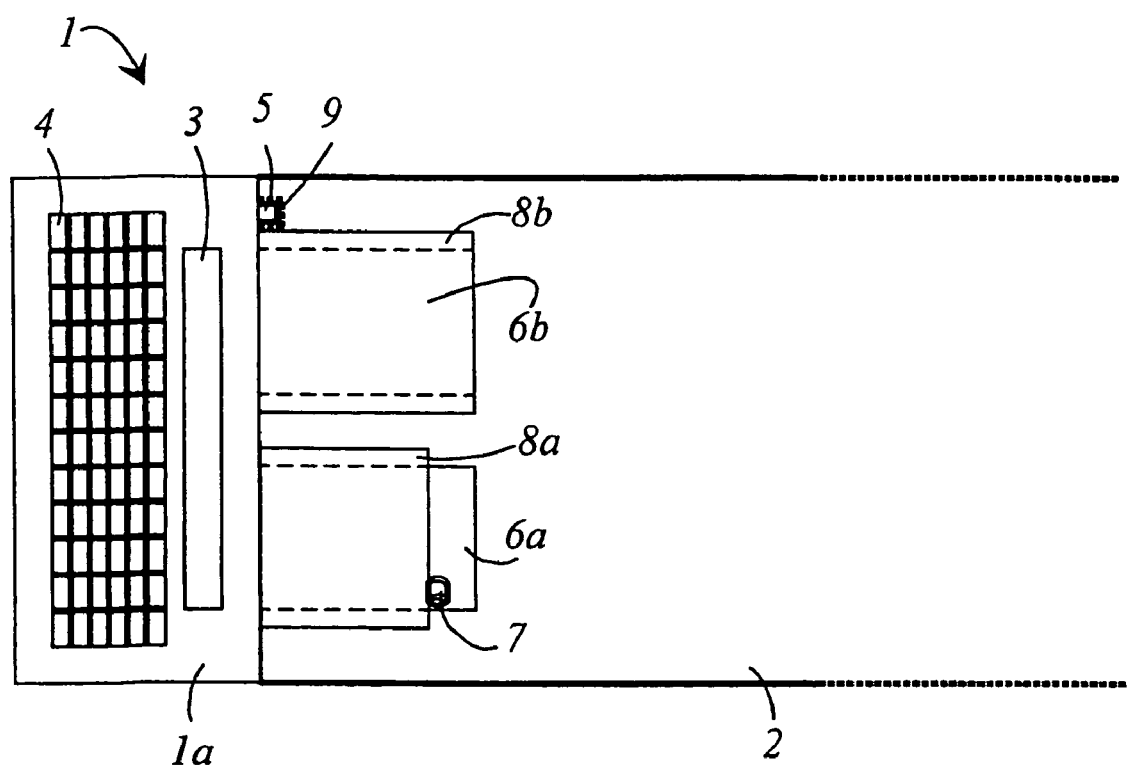
FIG. 2 schematically depicts the lamp housing and the remainder of the measurement arrangement in the connected state.

FIG. 2 shows lamp housing 1 connected to remaining portion 2 of the measurement arrangement. A first and a second socket 8a and 8b, in which first and second hollow cylinder 6a and 6b are respectively guided, are likewise connected to lamp housing 1 in order to guide and stabilize lamp housing 1. A first contact 9 is furthermore provided on remaining portion 2 of the measurement arrangement, for guidance and to create the electrical contact. First and second socket 8a and 8b are open at the end facing away from front side 1b of lamp housing 1, in order to transmit light of the illumination sources. When lamp housing 1 is inserted into remaining portion 2 of the measurement arrangement, an effective correlation is created between limiting stop 7 and at least one installation element (see FIGS. 4 and 5) in remaining portion 2 of the measurement arrangement. As a result, a defined orientation and alignment of the lamp housing with respect to remaining portion 2 of the measurement arrangement is achieved. When limiting stop 7 is effectively correlated with the installation element, any movement of lamp housing 1 in the guidance direction, i.e. relative to remaining portion 2 of the measurement arrangement, is thus prevented.

Figure 3:
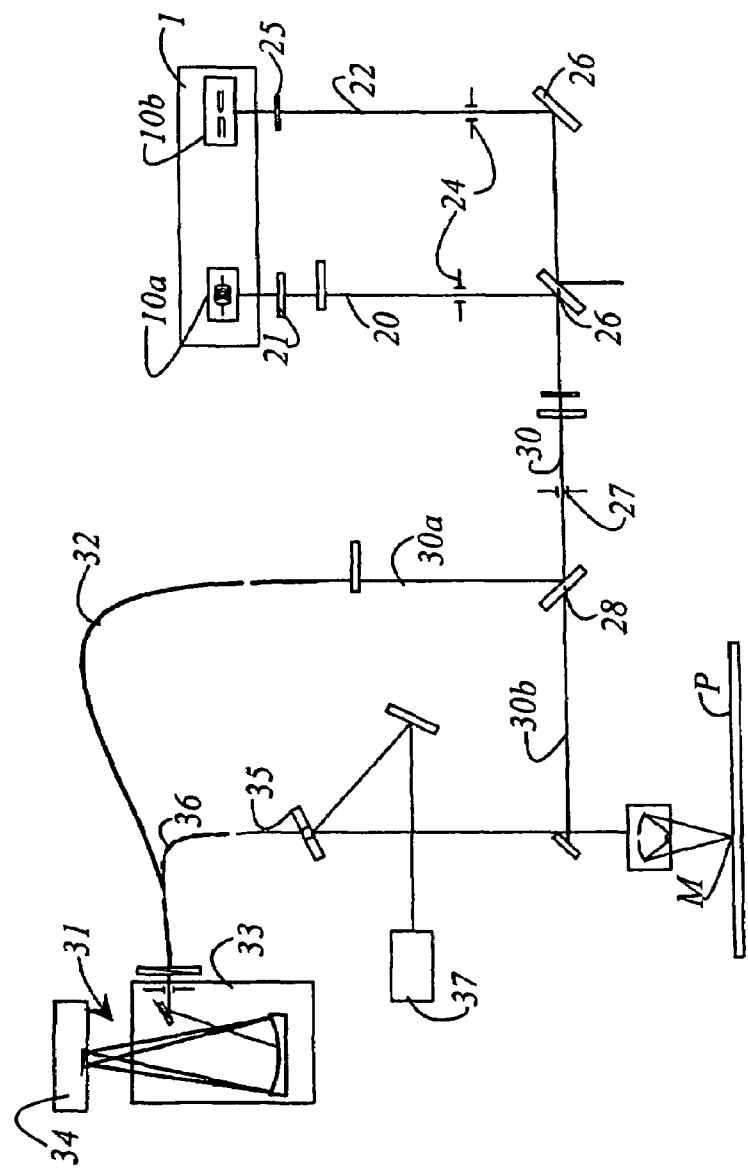
FIG. 3 schematically depicts the construction of a layer thickness measuring instrument with the lamp housing inserted.

FIG. 3 schematically depicts the construction of the measurement arrangement, which is embodied as an instrument for layer thickness measurement. Lamp housing 1 is connected to the remaining portion of measurement arrangement 2. A first and a second illumination source 10a and 10b are present in lamp housing 1. First illumination source 10a is a halogen lamp that emits, into a first illumination beam path 20 defined by measurement arrangement 2, light in the region between approximately 400 nm and approximately 800 nm that is visible to the human eye. Other wavelengths are filtered out by a front-mounted UV blocking filter 21. Second illumination source 10b is a deuterium lamp which emits light into a second illumination beam path 22. First and second illumination beam paths 20 and 22 are each shaped by a stop 24. Also provided in second illumination beam path 22 is a shutter 25 that interrupts second illumination beam path 22 in controlled fashion. First and second illumination beam paths 20 and 22 are combined by optical means 26 into a combined beam path 30. Combined beam path 30 passes through a field stop 27 and then strikes a beam splitter 28 in the form of a semitransparent deflection mirror. The measurement light beam of combined beam path 30 is divided by beam splitter 28 into a reference light beam 30a and a subject light beam 30b. The former is conveyed by means of a light guide 32 directly to an evaluation device 31, whereas subject light beam 30b is directed first onto a measurement location M on the surface of a sample P. Subject light beam 30b reflected from measurement location M is then likewise conveyed to evaluation device 31.

Evaluation device 31 encompasses a spectrograph 33 whose spectrum is directed onto the receiving matrix of a CCD detector 34.

Subject light beam 30b reflected from measurement location M, after passing through a pinhole mirror 35 and a further light-guiding device 36 that is likewise embodied as a light guide, reaches the spectrograph 33. Pinhole mirror 35 is of semitransparent configuration, so that a portion of subject light beam 30b can be diverted by it for further examination or observation purposes. The light diverted by pinhole mirror 35 is coupled into a device 37 for visual display. This is, for example, a color CCD video camera that serves to display on a monitor the region of the sample surface that is to be examined, for example in order to allow visual selection of a portion to be monitored or in order to observe the measurement operation. The image signal that is obtained can furthermore be recorded for the purpose of additional process monitoring.

Figure 4:
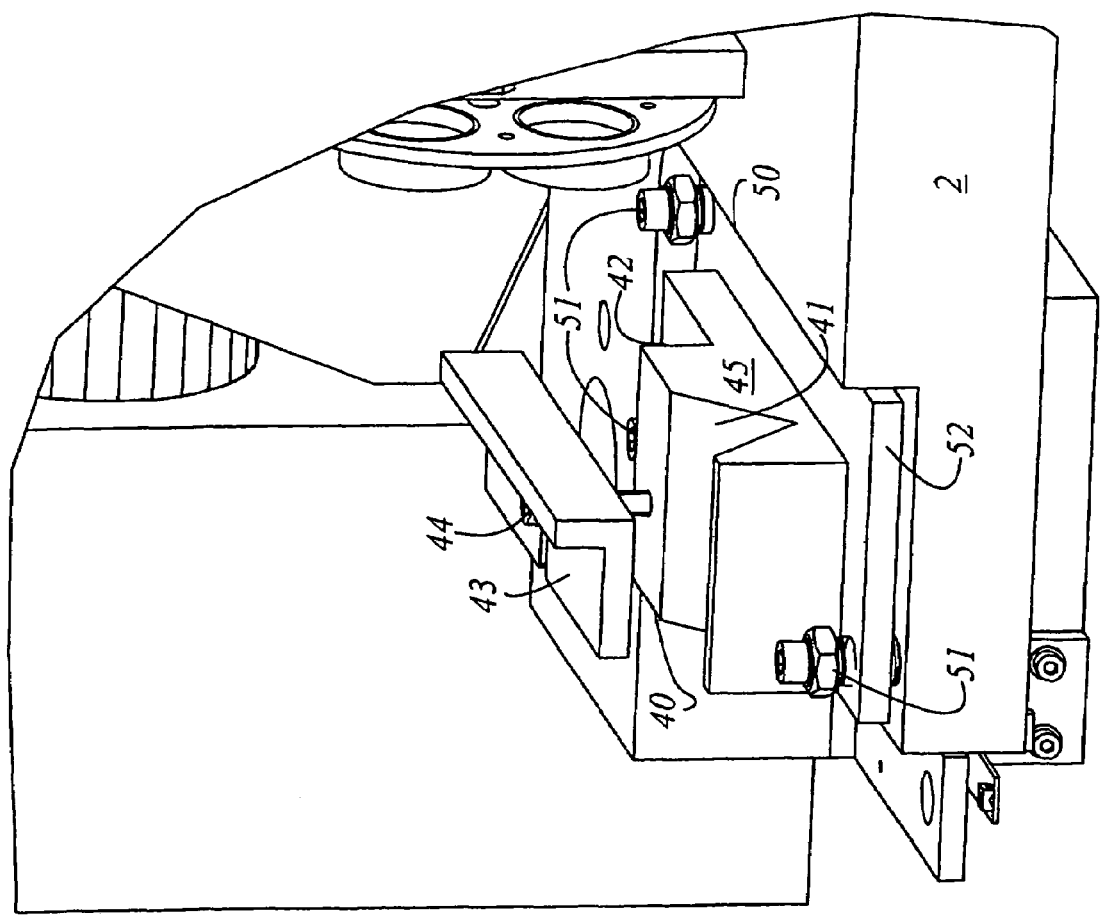
FIG. 4 is a perspective view of a concrete embodiment of a coupling point for a lamp housing onto a layer thickness measuring instrument.

FIG. 4 is a perspective partial view of a layer thickness measuring instrument without a lamp housing 1 in effective correlation with an installation element 40. Installation element 40 encompasses a block in which a notch 41 and a stop 42 are embodied. When lamp housing 1 having the two illumination sources 10a and 10b is inserted into measurement arrangement 2, first and second sockets 8a and 8b each rest against installation element 40, first socket 8a resting in notch 41 and second socket 8b against stop 42 (see FIG. 5).

For prevention of any movement of lamp housing 1 upward away from the guidance direction or any tilting, a plate 43 is mounted above installation element 40. Said plate 43 is designed so that it also limits the upward movement of sockets 8a and 8b. A smaller plate that covers only one of sockets 8a or 8b would suffice, but in the manner shown here the forces are more homogeneously distributed. Plate 43 is pressed immovably onto first and second socket 8a and 8b by means of a screw 44 that is joined to installation element 40. Installation element 40 is embodied on a solid plate 52 that rests against a precision edge 50 of measurement arrangement 2. Several attachment elements 51, with which plate 52 and thus installation element 40 can be aligned exactly with respect to measurement arrangement 2, are provided.

Figure 5:
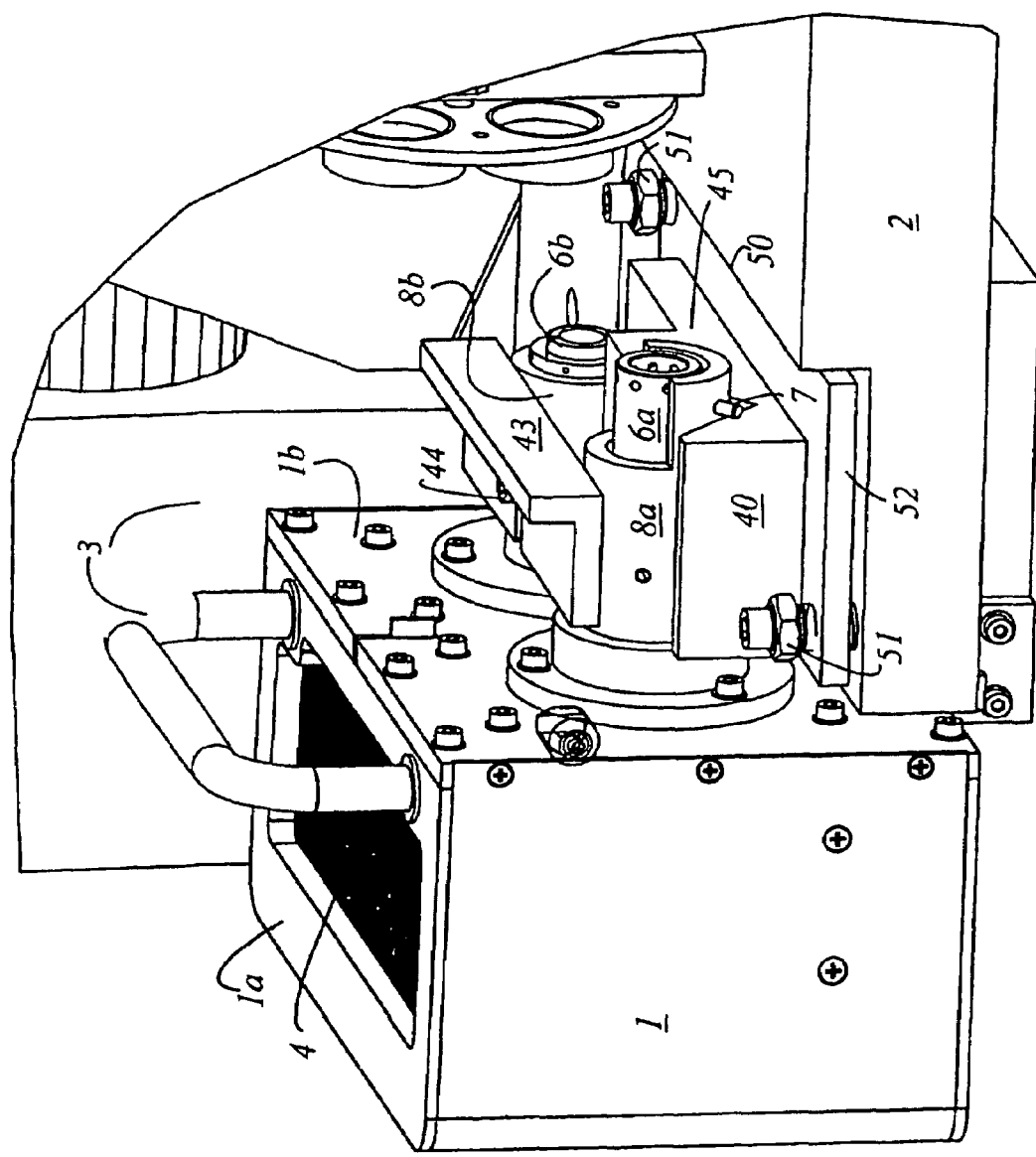
FIG. 5 is a perspective view of a concrete embodiment of the coupling point for a lamp housing onto a layer thickness measuring instrument, a lamp housing being connected to the coupling point.

FIG. 5 depicts the same perspective view of measurement arrangement 2 as in FIG. 4, lamp housing 1 being connected to measurement arrangement 2. The manner in which installation element 40 limits the movement of sockets 8a and 8b is clearly visible. First socket 8a of lamp housing 1 rests in notch 41, and second socket 8b rests against stop 42 of installation element 40.

First socket 8a is furthermore equipped with a limiting stop 7, projecting from it, which also suppresses movement opposite to the guidance direction. Limiting stop 7 is in contact with a front surface 45 of installation element 40. Limiting stop 7 can come into contact with front surface 45 only when lamp housing 1 has been slid in as far as possible, i.e. when no further movement in the guidance direction is possible. Lamp housing 1 is thus immobilized in all spatial directions. Insertion and removal require only a few actions that demand few technical resources.

Alignment of illumination sources 10a and 10b is eliminated according to the present invention, and measurement arrangement 2 can be put back into service immediately after the insertion of lamp housing 1. Illumination sources 10a and 10b are prealigned in lamp housing 1 in such a way that the beam paths defined by hollow cylinders 6a and 6b provided on lamp housing 1 coincide with first and second illumination beam paths 20 and 22 defined by measurement arrangement 2. Sockets 8a and 8b, limiting stop 7, notch 41, stop 42, and front surface 45 coact appropriately for that purpose. Notch 41, stop 42, first and second sockets 8a and 8b, solid plate 52 of installation element 40, and the edge of measurement arrangement 2 are precisely fabricated in order to achieve defined positioning of lamp housing 1.

What is claimed is:

1. An optical measurement system, comprising:
a measurement arrangement defining at least one illumination beam path;
a lamp housing having first and second illumination sources for delivering at least one measurement light beam into the at least one illumination beam path of the measurement arrangement;
an installation element connecting the lamp housing detachably to the measurement arrangement, wherein the first or the second illumination source is prealigned in the lamp housing such that the measurement light beam of the first and second illumination sources coincides with the at least one illumination beam path of the measurement arrangement;
first and second sockets on a front side of the lamp housing, wherein the first and second sockets are associated respectively with the first and second illumination sources; and
first and second hollow cylinders guided respectively in the first and second sockets, wherein light is guidable from the first and second illumination sources from the lamp housing through the first and second hollow cylinders to the measurement arrangement.

2. The optical measurement system as defined in claim 1, wherein at least one contact in a form of a socket and at least one further contact in a form of a pin are provided on the measurement arrangement in order to create an electrical contact between the lamp housing and the measurement arrangement.

3. The optical measurement system as defined in claim 1, wherein the installation element has a front surface against which rests a limiting stop provided on the first socket.

4. The optical measurement system as defined in claim 1, further comprising a handle mounted on the lamp housing that facilitates insertion of the first and second sockets into the installation element.

5. The optical measurement system as defined in claim 1, wherein the installation element comprises a block in which a notch and a stop are embodied.

6. The optical measurement system as defined in claim 5, wherein the first socket rests in the notch and the second socket rests against the stop; and
wherein the first and second sockets are immovably pressed with a plate onto the notch and into the stop, respectively.

7. The optical measurement system as defined in claim 6, wherein the plate is brought into contact with the first and second sockets by a screw joined to the installation element and thus retains the lamp housing in the installation element.

8. An optical measurement system comprising:

a measurement arrangement defining at least one illumination beam path;

a lamp housing having at least one illumination source for delivering at least one measurement light beam into the at least one illumination beam path of the measurement arrangement;

an installation element connecting the lamp housing detachably to the measurement arrangement, wherein the at least one illumination source is prealigned in the lamp housing such that the measurement light beam of the at least one illumination source coincides with the at least one illumination beam path of the measurement arrangement;

first and second sockets on a front side of the lamp housing; and a handle mounted on the lamp housing that facilitates insertion of the first and second sockets into the installation element.

9. The optical measurement system as defined in claim 8, wherein the at least one illumination source comprises first and second illumination light sources, and
wherein the first and second sockets are associated respectively with the first and second illumination light sources.

\* \* \* \* \*